(12) United States Patent
Melikyan et al.

(10) Patent No.: US 12,636,122 B1
(45) Date of Patent: May 26, 2026

(54) METHOD OF LAYERING COMPOSITE TOOTH RESTORATION ACCORDING TO A CONCEPT OF TEMPERATURE BALANCE AND DEVICES FOR ITS IMPLEMENTATION

(71) Applicants: Melikset Litvinovich Melikyan, New York, NY (US); Karine Meliksetovna Melikyan, New York, NY (US)

(72) Inventors: Melikset Litvinovich Melikyan, New York, NY (US); Karine Meliksetovna Melikyan, New York, NY (US); Garegin Meliksetovich Melikyan, Moscow (RU)

( * ) Notice: Subject to any disclaimer, the term of this patent is extended or adjusted under 35 U.S.C. 154(b) by 722 days.

(21) Appl. No.: 17/551,420

(22) Filed: Dec. 15, 2021

(51) Int. Cl.
A61C 5/55 (2017.01)
A61C 5/62 (2017.01)
A61B 50/20 (2016.01)

(52) U.S. Cl.
CPC .................. A61C 5/55 (2017.02); A61C 5/62 (2017.02); *A61B 2050/21* (2016.02)

(58) Field of Classification Search
CPC .......... A61C 5/55; A61C 5/62; A61B 2050/21
See application file for complete search history.

(56) References Cited

U.S. PATENT DOCUMENTS

| | | | | |
|---|---|---|---|---|
| 4,895,516 A | * | 1/1990 | Hulten ............... | A61C 13/0003 264/16 |
| 6,221,931 B1 | * | 4/2001 | Sakuma ................. | A61K 6/887 428/404 |
| 2012/0244496 A1 | * | 9/2012 | Jefferies ................... | A61C 3/06 433/142 |
| 2015/0230883 A1 | * | 8/2015 | Yumiyama ............... | A61C 3/02 433/166 |

* cited by examiner

*Primary Examiner* — Yogesh P Patel

(57) ABSTRACT

This invention relates to medicine, more particularly to dentistry, more specifically to a method of layering composite tooth restoration and means for its implementation with the use of a concept of temperature balance by M. L. Melikyan.

The inventive method of the layering composite tooth restoration is proposed which is implemented with the use of a syringe for heating of composite material, acid, polishing paste and a vessel for adhesive heating, a hydro-thermic heating device for heating working parts of restoration instruments, and a magnetic-panoramic stand for panoramic disposition and holding of medical instruments.

3 Claims, 16 Drawing Sheets

30

$110^0$

20

10

13

12

14

11

15

10

13

12

14

11

15

FIG. 3A
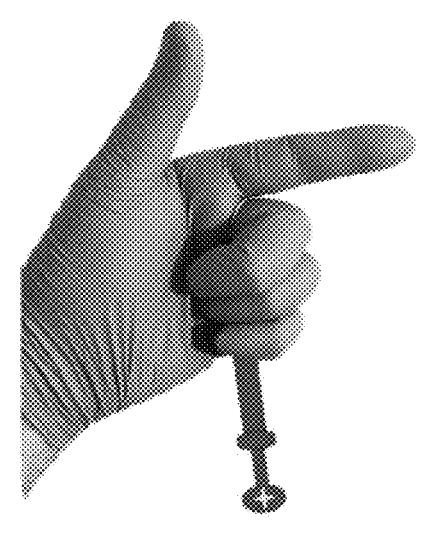
FIG. 3B
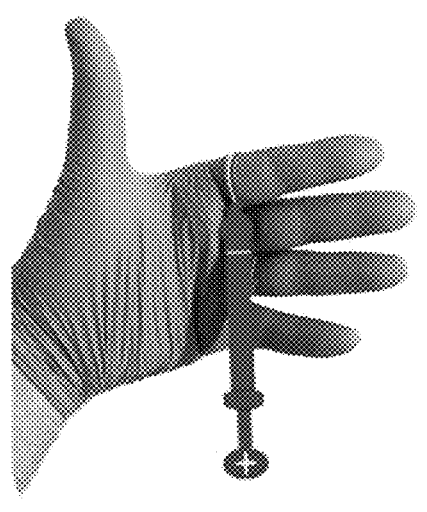
FIG. 4A
FIG. 4B

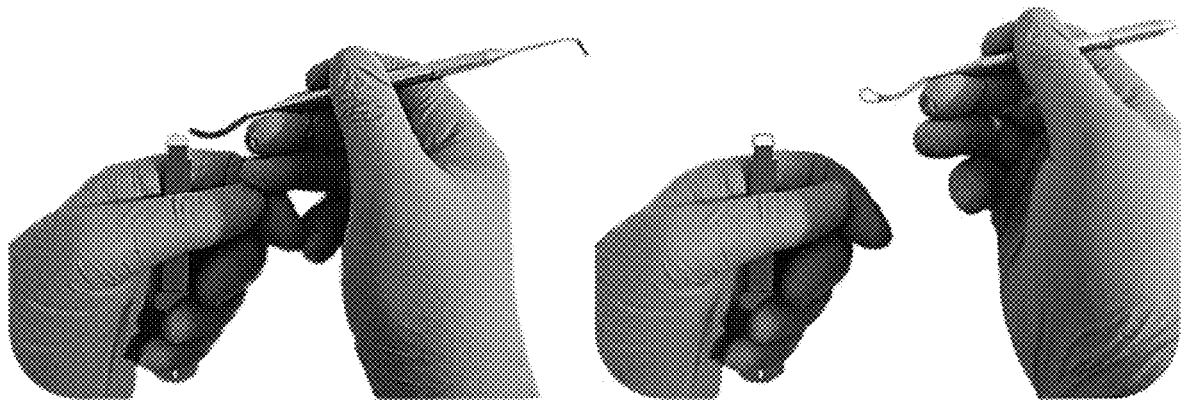
FIG. 7A                                              FIG. 7B
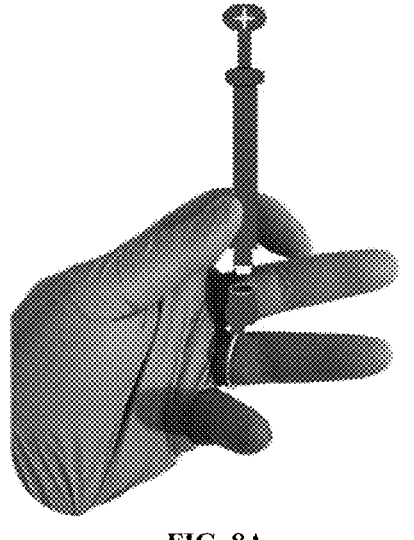
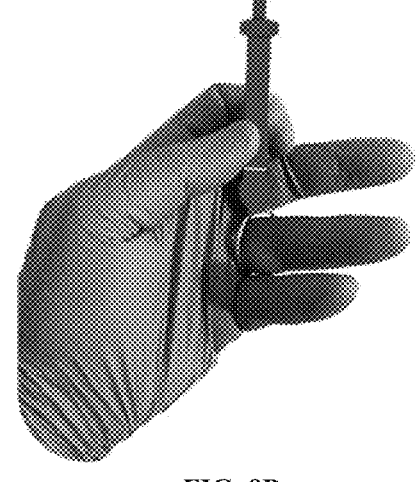
FIG. 8A                                              FIG. 8B 21  22        23  24  25  26                    20

21

22

27

21  22  23  24  25  26  27  20

21  27  22  20

31

31

33

30

120⁰

30

140⁰

20

METHOD OF LAYERING COMPOSITE TOOTH RESTORATION ACCORDING TO A CONCEPT OF TEMPERATURE BALANCE AND DEVICES FOR ITS IMPLEMENTATION

TECHNICAL FIELD OF THE INVENTION

This invention relates to medicine, more particularly to dentistry, more specifically to a method of layering composite tooth restoration and devices for its implementation according to a concept of temperature balance by M. L. Melikyan.

DESCRIPTION OF THE RELATED ART

Known from the prior art is a heating device (U.S. Pat. No. 4,092,138) that is configured for the storage of instruments, used by dental practitioners, at a temperature that is the best for their further use. The heating device comprises a hot section in which a flat topside surface is used to place the dental instruments for ensuring their heating to the prescribed temperature.

A disadvantage of the proposed heating device is the fact that the dental instruments cannot be heated to high temperatures since it is difficult for a dental practitioner to pick up the high-heated instruments from the high-heated surface. Thus the low-heated instruments shall quickly lose heat and give a short time for manipulation with them.

In addition, a heating device (U.S. Pat. No. 4,492,840) that is configured to heating of metal dental laboratory instruments and medical supplies is known from the prior art. The proposed device ensures heating at the expense of electric induction.

A disadvantage of the said device is that a dental practitioner or assistant has to wait for heating while keeping the medical instrument in the heating zone. In addition, the said procedure should be carried out separately with each medical instrument to be heated which slows down the dental practitioner working process.

Furthermore, composite materials are used during the tooth restoration along with the restoration instruments. It is known that heating of composite material to certain temperatures improves its physical and mechanical properties, in particular, increases the material ductility, plasticity, and improves the consistency homogeneity.

Many medical heating devices for a preliminary heating of composite materials are known at present. For example, known is a heating device "Dental AR Heat Composite Warmer Dental" comprising a heating housing with holes in which a syringe is inserted for heating its content. Apart from the specialized heating devices, the composite material can be heated by means of placing it into hot water, under an electric filament lamp, or by using a microwave.

The common disadvantage of the said known solutions is the fact that the composite material is repeatedly subjected to the cyclic impacts of the changing temperatures which result in thermal-cycle stress leading to different complications.

It is worth noting that exposure of an unpolymerized composite material to light initiates premature polymerization where the atmospheric oxygen acts as an inhibitor. Whereas it should be taken into account that the user actions, such as removal of a cap from the syringe with a composite material, sampling a composite material portion from a syringe nozzle, and closing the syringe, are performed with the use of both hands of the user. In particular, the left-hand holds the syringe with the composite material while the right-hand holds the instrument for sampling the composite material portion. Further, the right hand is used to remove the cap from the syringe body, it is moved to the left hand while the right hand is used to extract the composite material portion. After extraction of the composite material portion using the right hand which holds the composite material extracted portion, the syringe with the composite material shall be closed.

The traditional technique of extraction of the composite material portion from the syringe body requires many moves of the user's hands, and, besides making the very procedure of extraction of the composite material portion complicated, this increases the time interval of exposure of the composite material to light and atmospheric oxygen when the nozzle of the syringe body with the composite material is open and when the composite material portion is extracted from the syringe body.

Thus, there is a need to develop such a method of layering composite tooth restoration, which shall reduce the likelihood of complications. Further, there is a need to develop such a method, which shall comprise usage of the heated restoration instruments, and heated composite material, which shall contribute to the increase of the composite restoration functioning term.

Now, therefore, the object of this invention is to develop an effective method of layering composite tooth restoration and devices adopted to its implementation with the use of a concept of temperature balance by M. L. Melikyan.

SUMMARY OF THE INVENTION

In a first aspect, this invention relates to a syringe for heating a composite material, acid, or polishing paste used in a method of providing medical services according to the temperature balance concept.

According to the invention, the syringe comprises a body comprising a nozzle, a plunger configured to move inside the body squeezing a body content through the nozzle, a cap closing the nozzle, and a ring attached to a butt end of the cap, wherein the ring is configured to be put on a user's finger.

According to an embodiment, the ring of the syringe is configured to adjust its diameter and its attachment to the butt end of the cap is made as movable or rigid, detachable or non-detachable.

Configuration of the ring of the syringe, the diameter of which allows to put it on the finger, provides a securely hold of the syringe in the palm of the user thus ensuring the heating of the syringe content while all manipulations with the syringe can be performed using one hand. More particularly due to the fact that the ring is located directly on the butt end of the cap it is possible to hold the cap on the finger while the free fingers of the same hand can be used to remove the cap from the body and to close it with the cap after finishing extraction of a composite material portion. On the other hand, is free and can be used to work with the material. Thus one hand of the user ensures holding the syringe, it is heating with the warmth of the palm, and performance of manipulations related to opening and closing the cap while the other hand remains free.

In addition, since only some fingers of one hand are participating in holding the syringe, the free fingers of the same hand can also be engaged in holding additional instruments. For example, in the composite restoration process, when the user has extracted a required composite material portion from the syringe, the syringe is held with two fingers (ring finger and little finger) which makes it possible for the user to put both hands into use for other tasks at the same time that one of them is holding the syringe. Thus, the syringe can be held in the user's hand (palm) during the whole process of the composite restoration, which makes it possible to maintain the constant temperature of the composite material in the syringe.

It is worth noting that opening and closing of the syringe with one hand is performed in a shorter time as compared to the same actions performed with two hands since the necessity of putting the cap and the material extraction instrument from hand to hand is excluded. Thus, the duration of exposure to light and atmospheric oxygen for the material situated at the exit (nozzle) of the syringe body and for a material portion extracted from the composite material heating device is decreasing.

In the second aspect, this invention relates to a hydro-thermic heating device for heating a working part of a restoration instrument used in a method of providing medical services according to the temperature balance concept. According to the invention, the hydro-thermic heating device comprises a housing comprising a liquid chamber, a heating element for the liquid chamber located under the liquid chamber, a switch-on indicator of the heating element, a temperature controller is configured to set a desired temperature of the heating element and an automatic switch is configured to maintain a preset temperature of the heating element.

The heating element for the liquid chamber, located under the liquid chamber, ensures uniform and quick heating of the liquid. The temperature controller makes it possible to set the temperature for the liquid chamber so that after bringing the liquid to the set temperature the automatic switch would ensure automatic disconnection of the heating element and its switching-on when the set temperature decreases.

In an embodiment, the hydro-thermic heating device can comprise a pod with the perforated bottom located inside the liquid chamber.

In the third aspect, this invention relates to a magnetic-panoramic stand for panoramic disposition and holding of medical instruments including the restoration instruments used in the method of providing medical services according to the temperature balance concept. According to the invention, the magnetic-panoramic stand comprises two pairs of legs, wherein each pair of the legs are connected to each other from one end using threaded studs so that each pair of the legs forms a bearing member of the stand, two stoppers containing two beams each of which is attached to a corresponding bearing member of the stand using the threaded studs and restricts movement of the legs relative to each other in each bearing member of the stand, a fixing beam which connects the bearing members of the stand with one another using the threaded studs and a magnet holder comprising a shaped metal housing and magnets located in it, wherein each end of the magnet holder is attached to the corresponding bearing member of the stand. It is worth noting that the magnetic-panoramic stand can comprise removable metal insulating plates, which are located on the magnet holder and designed to insulate the restoration instrument from the magnetic holder.

Installation of the magnetic-panoramic stand above the hydro-thermic heating device and availability of the magnets makes it possible to hold the restoration instruments above the hydro-thermic heating device so that only the working part of the restoration instruments is dipped into the liquid chamber. Dipping of only the working parts of the restoration instruments into the heated liquid chamber makes it possible to ensure their heating up to the desired temperature while the remaining parts of the restoration instruments are not heated or heated to a lower temperature, that is temperature of that part of the medical instrument which is dipped into the liquid chamber shall be higher compared to the non-submerged part.

In an embodiment, each end of the magnet holder is attached to the corresponding bearing member of the stand using a detachable connection.

In another embodiment, each end of the magnet holder is attached to the corresponding bearing member of the stand using the magnets installed inside the bearing members of the stand.

In a further embodiment, the magnetic-panoramic stand comprises a support configured to rotate the magnetic-panoramic stand in a horizontal plane and/or a vertical plane.

In the fourth aspect, this invention relates to a method of providing medical services according to the temperature balance concept wherein providing medical services is the layering composite tooth restoration. The method comprises heating an acid, a composite material and a polishing paste in corresponding syringes and heating an adhesive in a vessel for an adhesive, heating a working part of a restoration instrument in a hydro-thermic heating device using a magnetic-panoramic stand for panoramic disposition and reliable holding of the restoration instrument, wherein the magnetic-panoramic stand is configured to be installed above the hydro-thermic heating device so that only the working part of the restoration instrument is dipped into the hydro-thermic heating device, performing a tooth preparation using a water and air heated to a body temperature, extracting, from the corresponding syringe, an acid portion heated to the body temperature, applying the heated acid portion to a prepared tooth surface, then washing away the acid portion using the water heated to the body temperature and drying the tooth surface using an air heated to the body temperature, extracting, from the vessel for the adhesive, an adhesive portion heated to the body temperature, applying the heated adhesive portion to a dried tooth surface, blowing the adhesive portion using the air heated to the body temperature after which polymerization is performed, extracting, from the corresponding syringe, a first composite material portion heated to the body temperature using of the working part of the restoration instrument heated to the body temperature, applying the first heated composite material portion to a polymerized surface of an adhesive layer using the working part of the restoration instrument heated to the body temperature, and performing the polymerization after compacting the first heated composite material portion, extracting, from the corresponding syringes, a second and subsequent composite material portions heated to the body temperature using the working part of the restoration instrument heated to the body temperature, applying the heated second and subsequent composite material portions to a polymerized surface of the composite layer using the working part of the restoration instrument heated to the body temperature, and performing the polymerization after compacting the second and subsequent composite material portions, after grinding of last composite layer, extracting, from the corresponding syringe, a polishing paste portion heated to the body temperature, applying the heated polishing paste portion to a ground polymerized surface of the last composite material layer and performing a polishing.

In an embodiment, the syringe is heated in a palm wherein the syringe is held in the palm by a ring attached to a cap of the syringe.

In another embodiment, the vessel for the adhesive is heated in the palm wherein the vessel for the adhesive is held in the palm by a ring attached to a butt end of the vessel for the adhesive.

In the fifth aspect, the invention relates to a method of providing medical services according to the temperature balance concept. The method comprises using when interacting with a patient's body during medical care, a system approach, where all objects interacting with the patient's body, including instruments, fluids, and medical materials, are pre-heated to the generally accepted normal value of a body temperature before interaction with patient's body.

The inventive method ensures the constant temperature of the heated composite material which improves its yield, plasticity, marginal adaptation, and manipulation parameters which, in turn, considerably decreases the number of occurrences of large critical closed and strain restoration pores as well as critical zones in the composite restoration volume which is the main reason leading to the occurrence of cracks, micro-and-macro chipping of the composite restoration. Thus, said possibility makes it possible to obtain a high-quality restoration with prolonged service life.

The present invention makes it possible to exclude thermal cycling stress of the composite material in process of the layering composite tooth restoration, to perform all stages of the layering composite tooth restoration under the temperature balance conditions, to increase wear resistance and strength of the composite restoration due to decrease in viscosity and shrinkage causing high adaptation and marginal fit as well as the tough and strong micro-mechanical junction between the composite material and prepared cavity or the restored tooth surface. Further, the present invention makes it possible to perform the restoration within as short a time as possible. Thus, the present invention ensures a technical result in terms of simplification and acceleration of the process of the layering composite tooth restoration while ensuring the high quality of the performed restoration.

BRIEF DESCRIPTION OF THE DRAWINGS

The summary of the invention is explained in more detail with reference to the attached drawings:

FIG. 3A shows a syringe held by the open palm of the user, a ring of which located on the middle finger according to an embodiment of the invention.

FIG. 3B shows a syringe contacting with a small finger, a ring finger, and a middle finger when heating it according to an embodiment of the invention.

FIG. 4A shows a syringe held by the open palm of the user, a ring of which located on the forefinger according to an embodiment of the invention.

FIG. 4B shows a syringe contacting with a small finger, a ring finger, a middle finger, and a forefinger when heating it according to an embodiment of the invention.

FIG. 7A shows a position of a syringe in the user's hand when extracting material from the discharge opening of a nozzle channel by a restoration instrument according to an embodiment of the invention.

FIG. 7B shows a position of a syringe in the user's hand when extracting material from the discharge opening of a nozzle channel by a restoration instrument according to an embodiment of the invention.

FIG. 8A shows a position of a thumb and a forefinger prior to the attachment of a cap to a syringe body according to an embodiment of the invention.

FIG. 8B shows positions of a thumb and a forefinger after attachment of a cap to syringe body according to an embodiment of the invention.

DETAILED DESCRIPTION

One of the main reasons for the occurrence of complications during the composite tooth restorations is heat exchange, which is understood as heat transfer from a warmer body to a less heated one until their temperatures become equal wherein time is required for temperature equalization of the bodies.

When working on this invention, a concept of temperature balance by M. L. Melikyan during the layering composite tooth restoration with the aim of reducing the number of complications and increasing the functioning term of the composite restoration was first developed.

The concept of temperature balance by M. L. Melikyan during the composite tooth restoration represents the elimination of defects of hard tooth tissues and dental arch with the preliminary heating of water (for cooling the dentist's borer, wetting, and rinsing the mouth cavity), acid (etching gel), adhesive, working part of the restoration instruments, unpolymerized composite material, polishing paste and, where applicable, other materials used in the composite tooth restoration to the standard body temperature, in particular, 36.6° C.

According to the concept of temperature balance, a block for a preliminary heating of water to the body temperature (for cooling the dentist's borer, wetting, and rinsing the mouth cavity) is built into the dental treatment unit during the composite tooth restoration.

It is necessary to note that said concept of temperature balance according to M. L. Melikyan can be used not only in dentistry but also in other areas of medicine where consideration of temperature balance can be of practical value.

The inventive method for the layering composite tooth restoration using the concept of the temperature balance according to M. L. Melikyan, in compliance with embodiments of this invention, is realized with the use of a syringe for heating a composite material, an acid, or a polishing paste, a hydro-thermic heating device for heating working parts of restoration instruments and a magnetic-panoramic stand for the panoramic holding of medical instruments including the restoration instruments.

The syringe used for heating of the composite material, acid or polishing paste can have varied volumes and sizes depending on the substance for which it is intended and is described in more detail by a way of example of the syringe for unpolymerized composite material. The syringe for the unpolymerized composite material according to the invention (hereinafter referred to as composite material), in an embodiment, is used in dentistry, in particular, for the layering composite tooth restoration under conditions of the temperature balance.

The tooth restoration under conditions of the temperature balance is a restoration of a decayed tooth where the temperature of acid, adhesive, composite material, polishing paste, and the tooth is the same.

Figure 1A:
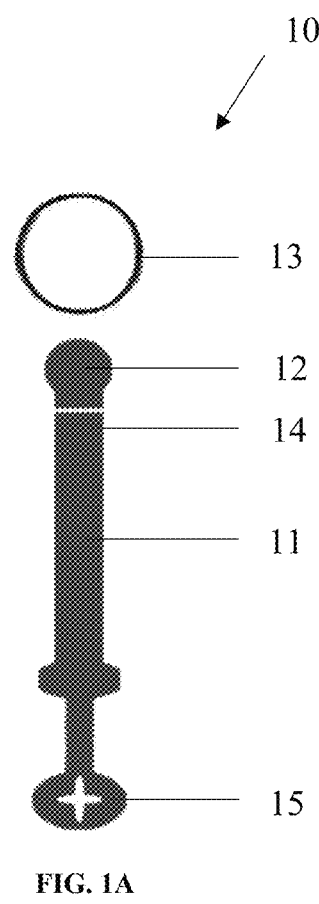
FIG. 1A shows a syringe with a ring detached from a cap according to an embodiment of the invention.
Figure 1B:
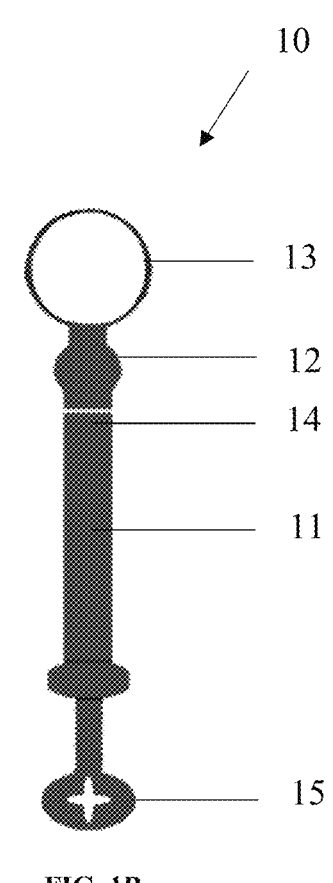
FIG. 1B shows a syringe with a ring attached to a cap according to an embodiment of the invention.

FIGS. 1A and 1B illustrate a syringe 10 comprising a body 11, closed by a cap 12 and a ring 13 attached to a butt end of the cap 12. Body 11 and cap 12 of the syringe are made of plastic and have a cylindrical shape. The ring has a diameter making it possible to put ring 13 on the user's finger. In a preferred embodiment, ring 13 is designed for putting on a ring finger, middle finger, or forefinger wherein selection of a finger for putting the ring 13 on it is made depending on the clinical situation. In a preferred embodiment, the diameter of ring 13 is fixed and selected to ensure the possibility of putting it on any finger of the user. In this case, the diameter of the ring 13 can be equal from 14 mm to 24 mm. Alternatively, the diameter of ring 13 can be adjusted by the user for his/her particular finger.

Ring 13 has a non-detachable rigid connection to cap 12 that is immovably connected to it. The non-detachable rigid connection of ring 13 to cap 12 ensures maximum control over the syringe when working with it and eliminates any possibility of their detachment. Alternatively, ring 13 can have a movable connection to cap 12 of the syringe, which makes it easier to put the ring on the finger. The ring 13 can also have a detachable connection to cap 12 making the syringe with ring portable in storage.

Ring 13 is made of metal owing to which it maintains the shape. Ring 13 can also be made of other materials, for example, plastic, which ensures maintaining the ring shape. Maintaining the ring shape is also ensured due to the ring width, varying from 4 mm to 10 mm, and thickness, varying from 2 mm to 4 mm. It is worth noting that the ring width and thickness are selected depending on the used material.

Figure 2A:
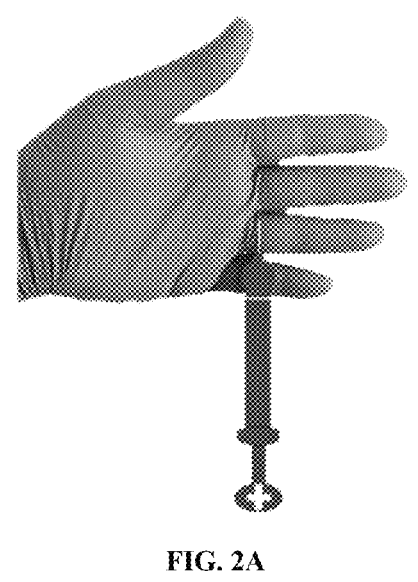
FIG. 2A shows a syringe held by the open palm of the user, a ring of which located on the ring finger according to an embodiment of the invention.
Figure 2B:
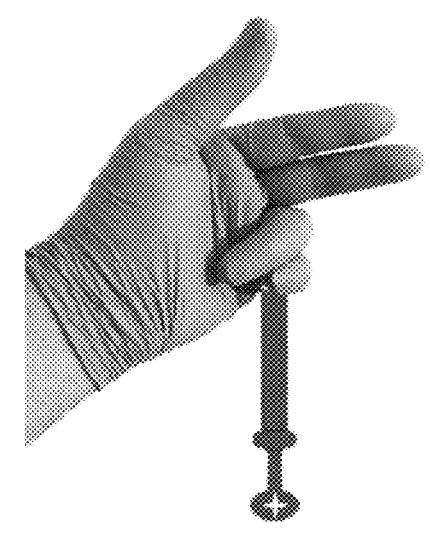
FIG. 2B shows a syringe contacting with a small finger and a ring finger when heating it according to an embodiment of the invention.

One of the main tasks during the layering composite tooth restoration is the elimination of thermal cycling stress during heating of an unpolymerized composite material, acid, adhesive, and polishing paste. The availability of ring 13 in the proposed design makes it possible to firmly hold syringe 10 in the user's hand during the whole process of the composite tooth restoration thus excluding the thermal cycling stress. In particular, ring 13 is put on the ring finger of the left hand (if the use is right-handed) until tight so that the syringe with the composite material (or acid or polishing paste) is suspended in the palm (the syringe primary position) and cap 12 of the syringe is on the lower phalanx of the little finger as shown in FIG. 2A. Further, the user bends the little finger and ring finger in the direction of the palm so that the syringe cap and nozzle are pressed to the palm by the upper, middle, and lower phalanges of the ring finger and little finger while thumb, forefinger, and middle finger are remaining free as shown in FIG. 2B.

Thus, the composite material located at nozzle 14 of syringe 10 is heated up to the user's body temperature in a few minutes. In particular, heated is that composite material portion in the syringe, which corresponds to the width of lower phalanges of the ring finger and little finger, clasping the syringe. Owing to the said position of the syringe in the hand, a part of the composite material is heated during the whole process of the composite tooth restoration while the remaining composite material portion is not heated which increases the composite material lifetime.

The segmental heating of the composite material in the syringe is possible in the range from 2 cm to 6 cm from the nozzle 14 sides (FIGS. 2A-4B). The size of the composite material heated segment depends on the position of the syringe in the user's palm. In particular, segment I, from 1.5 cm to 2.5 cm, is achieved through putting the ring on the ring finger and clasping the syringe by the little finger and ring finger (FIGS. 2A-2B): segment II, from 2.5 cm to 4 cm, is achieved through putting the ring on the middle finger and clasping the syringe by the little finger, ring finger and middle finger (FIGS. 3A-3B); segment III, form 4 cm to 6 cm, is achieved through putting the ring on the forefinger and clasping the syringe by the little finger, ring finger, middle finger, and forefinger (FIGS. 4A-4B). Thus, a simple, handy, and efficient method of the segmental heating of the composite material in the syringe is attained.

Figure 5A:
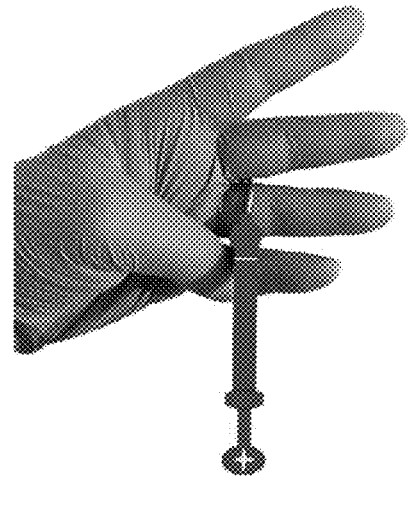
FIG. 5A shows a position of a syringe when changing over from initial position to working position according to an embodiment of the invention.
Figure 5B:
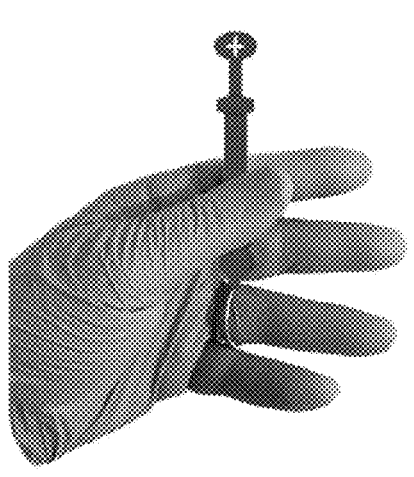
FIG. 5B shows a position of a syringe in the user's hand in a working position according to an embodiment of the invention.

Syringe 10 is moved from the primary position to the working position to extract a heated composite material portion (FIGS. 5A-5B). For this purpose, the little finger and ring finger are opened. The syringe becomes suspended on the ring finger. The syringe is turned 180° upwards using the back surface of the left-hand thumb as shown in FIG. 5A.

At the preparation stage, prior to extraction, the user has a possibility, without removing the cap 12, to slowly turn a plunger 15 of the syringe 10 clockwise by half turn for squeezing the composite material from the cylindrical part of body 11 of the syringe to the nozzle 14 and further through the cylindrical channel of the nozzle 14 to the discharge opening. The preparation stage ensures the reduction of exposure of the composite material surface located at the nozzle discharge opening to light and atmospheric oxygen.

Figure 6A:
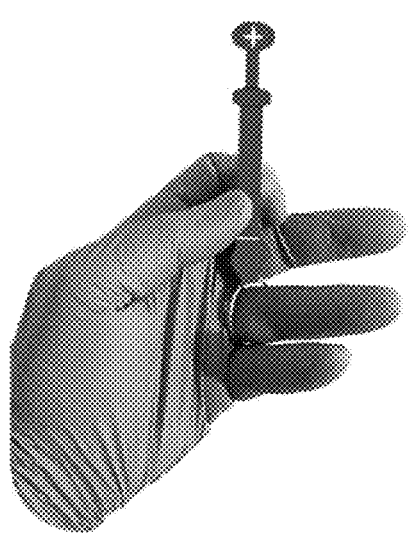
FIG. 6A shows a position of a thumb and a forefinger prior to detachment of a syringe from a cap according to an embodiment of the invention.
Figure 6B:
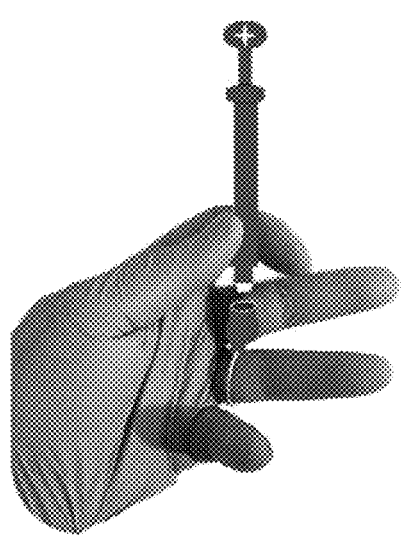
FIG. 6B shows a position of a thumb and a forefinger after detachment of a syringe from a cap according to an embodiment of the invention.

It is worth noting that when extracting a composite material portion using the traditional method of layering composite tooth restoration, the user works with both hands. The design proposed in this invention allows detaching the body 11 of the syringe 10 from the cap 12 using the thumb and forefinger of the left hand so that the cap 12 fixed on the ring 13 remains on the ring finger as shown in FIGS. 6A-6B. Using the restoration instrument, the user extracts a heated composite material portion from the discharge opening of the channel of the nozzle 14 (FIGS. 7A-7B) after which body 11 of the syringe 10 is installed back into cap 12 using the thumb and forefinger of the same left hand (FIGS. 8A-8B). Further, the syringe is moved from the working position back to the primary position.

Figure 9A:
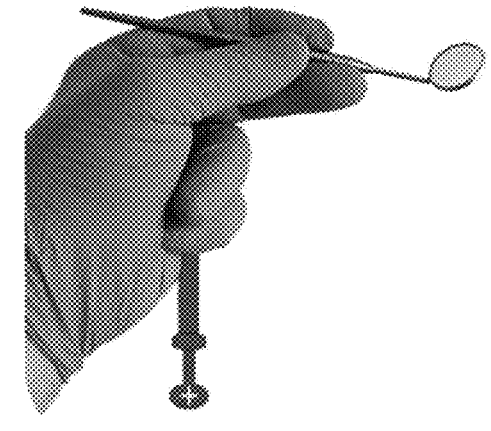
FIG. 9A shows a position of a syringe in the user's hand while holding a mirror with a thumb, a forefinger, and a middle finger according to an embodiment of the invention.
Figure 9B:
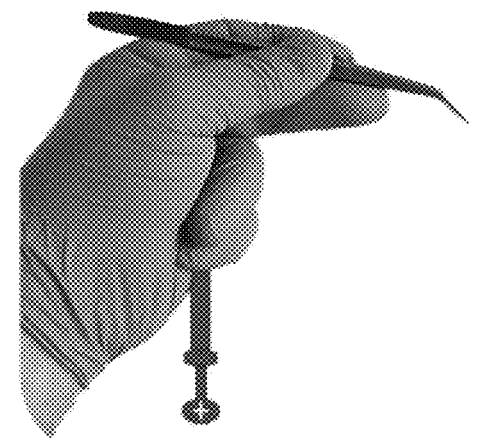
FIG. 9B shows a position of a syringe in the user's hand while holding a forceps with a thumb, a forefinger, and a middle finger according to an embodiment of the invention.

Thus ring 13, put on the ring finger of the left hand, does not limit functions of the thumb, forefinger, and middle finger. In process of restoration the hand, holding the syringe, remains in working condition which makes it possible to carry out manipulations with the necessary instruments, for example as shown in FIGS. 9A-9B. Thanks to the fact that the syringe, held in the hand, does not interfere with performing different manipulations, the user can hold it in the hand from the beginning to the end of the tooth restoration. Thus, the possibility of maintaining the constant temperature of the composite material during the whole restoration is ensured. Maintenance of the composite material's constant temperature excludes its thermal cycling stress as compared with the prior art solutions which envisage periodic heating of the composite material in the restoration process. Thus, the composite material quality is maintained and, correspondingly, its lifetime is increased.

Besides, the use of only one hand to remove and install the cap on the syringe body makes it easier and, thus, accelerates the process of extraction of the composite material portion from the syringe. Thus, the design proposed in this invention makes it possible to minimize the time of exposure of the extracted portion and the composite material surface at the nozzle inlet opening to light and atmospheric air.

It is preferable that extraction of the composite material portion is carried out at a short distance between the syringe and the restored tooth. Reducing the distance minimizes the time of exposure of the preheated composite material portion to light and atmospheric oxygen.

It is worth noting that properties of the non-heated composite material such as yield, plasticity, marginal adaptation, and manipulation parameters are not the best. During the tooth, restoration without preliminary heating of the composite material heat is transferred from the tooth to the composite material. However, in this case, the composite material portion is heated very slowly. Thus until polymerization (the final stage) the said properties of the non-heated composite material do not improve significantly.

The syringe 10 according to the invention makes it possible to ensure heating of the composite material up to the body temperature, which improves its yield, plasticity, and marginal adaptation and manipulation parameters. Thus, the syringe design proposed in this invention makes it possible to carry out the layering composite tooth restoration under conditions of the temperature balance, which reduces the number of complications and increases the composite restoration lifetime.

When working with the heated composite material and to maintain its temperature, the heated working part of the restoration instrument is used.

Figure 10:
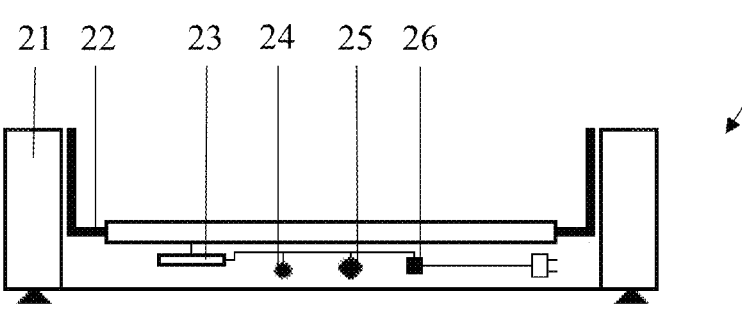
FIG. 10 shows a longitudinal section of a hydro-thermic heating device for heating the working part of a restoration instrument according to an embodiment of the invention.

The hydro-thermic heating device is used for heating working parts of the restoration instruments. The hydro-thermic heating device 20 is shown in FIG. 10 and comprises a housing 21 were located a liquid chamber 22, a heating element 23 for liquid chamber 22 located under the liquid chamber 22, an indicator 24 of switching-on of the heating element for the liquid chamber 22, a temperature controller 25 allowing the user to set the desired temperature of the heating element for the liquid chamber 22 and an automatic switch 26 configured to maintain the set temperature of the liquid chamber 22.

Figure 11:
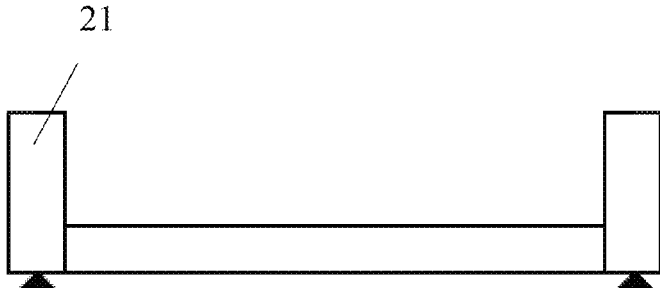
FIG. 11 shows a longitudinal section of a housing of a hydro-thermic heating device according to an embodiment of the invention.

The housing of the hydro-thermic heating device 20 is designed in the form of a rectangle with length from 23 cm to 25 cm, width from 5 cm 10 cm, and height from 7 cm to 8 cm (FIG. 11). The dimensions are optimal for arranging the housing 21 on a dentist's working table, in particular, the housing 21 of the dimensions occupies minimum space and does not interfere with the dental practitioner's work. The thickness of a lower part of the housing 21 is from 3 cm to 4 cm which makes it possible to arrange the heating element 23 and the temperature controller 25 in it. The housing can also have rubber legs to prevent sliding on the table.

Figure 12:
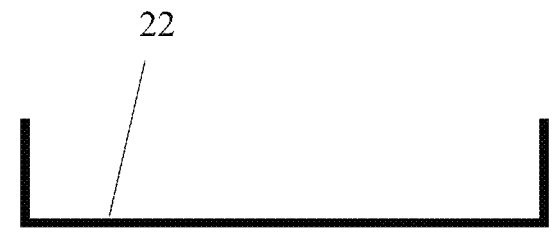
FIG. 12 shows a longitudinal section of a liquid chamber of a hydro-thermic heating device according to an embodiment of the invention.

The liquid chamber 22 of the hydro-thermic heating device is designed for keeping liquid, for example, distilled water, into which the working parts of the restoration instruments are dipped (FIG. 12). The liquid chamber 22 has the rectangular form following the housing form with length from 19 cm to 20 cm, width from 4 cm to 5 cm, and height from 4 cm to 5 cm. Liquid chamber 22 is made of high-quality medical stainless steel, the wall thickness is from 1 mm to 1.5 mm. The liquid chamber 22 and the housing 21 can have different forms, for example, oval, round, square, triangle, or any other form adapted to the dentist's table form. Dimensions of housing 21 and liquid chamber 22 can be decreased or increased.

Figure 13:
FIG. 13 shows a longitudinal section of a pod of a hydro-thermic heating device according to an embodiment of the invention.
Figure 14:
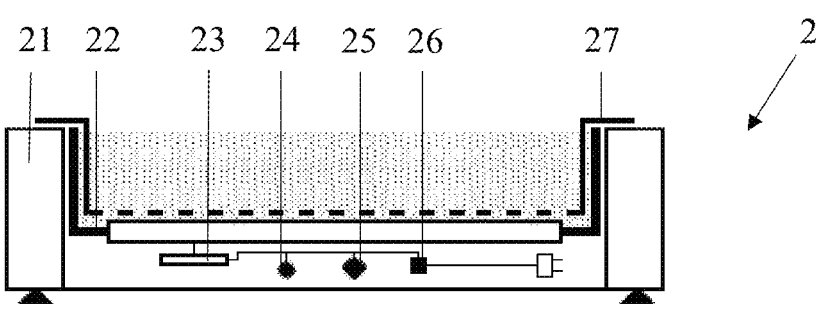
FIG. 14 shows a longitudinal section of a hydro-thermic heating device for heating the working part of a restoration instrument comprising a pod according to an embodiment of the invention.
Figure 15:
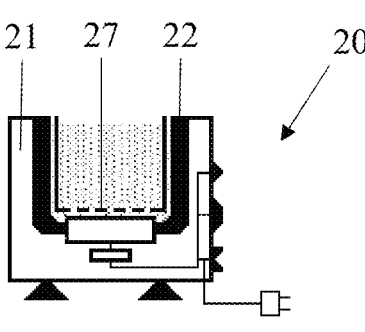
FIG. 15 shows a cross-section of a hydro-thermic heating device for heating the working part of a restoration instrument comprising a pod according to an embodiment of the invention.

Besides, pod 27 is located at the chamber bottom (FIG. 13) following its form. The length, width, and height of the rectangular pod 27 are 0.5 cm smaller than the dimensions of the liquid chamber while pod 27 thickness is within the limits of 1.5 cm. pod 27 has perforation and can be made of plastic or high-quality medical stainless steel. To remove pod 27 from the liquid chamber there are handles on its sidewalls, which are made of the same material as the material of pod 27. FIGS. 14 and 15 show longitudinal and cross-sections of the hydro-thermic heating device with the pod for heating of the restoration instrument working part.

Figure 16:
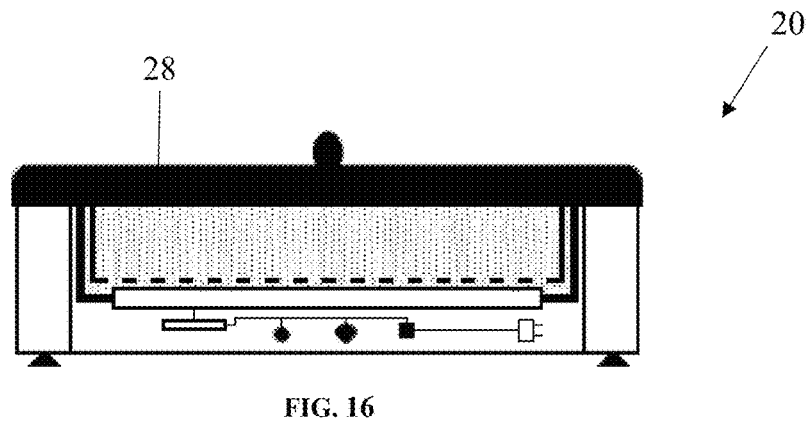
FIG. 16 shows a longitudinal section of a hydro-thermic heating device with a closed lid for use during chemical and thermal sterilization of medical and restoration instruments according to an embodiment of the invention.

The hydro-thermic heating device can also have a lid 28 as shown in FIG. 16. The lid 28 is used for closing the hydro-thermic heating device, in particular the liquid chamber 22, during chemical and thermal sterilization of the restoration instruments or any other medical instruments.

The heating element 23 for liquid chamber 22 is located in the bottom of housing 21 under the liquid chamber 22 and configured to a possibility of its heating (FIG. 14). The location of the heating element 23 for the liquid chamber ensures uniform heating of the liquid chamber 22 and, as a result, of working parts of the restoration instruments which are dipped into it.

The temperature controller 25 of the hydro-thermic heating device 20 allows the user to set the desired temperature of the heating element 23 for the liquid chamber. The temperature controller 25 maintains the temperature of the liquid chamber 22 with the use of the built-in automatic switch 26, which automatically switches off the heating element 23 after the fluid is heated to the set temperature and, correspondingly, switches it on when the temperature lowers below the set threshold. The temperature controller 25 makes it possible to heat the liquid in the liquid chamber from 36° C. to 100° C.

In a preferred embodiment, to heat the restoration instrument working part, the hydro-thermic heating device 20 is set to a mode ensuring heating of the liquid chamber 22 up to 75° C. When heating the liquid chamber 22, the indicator 24 light of switching-on of the heating element 23 for the liquid chamber 22 is on. Upon reaching the set temperature of liquid chamber 22, the heating element 23 for the liquid chamber is automatically switched-off and goes to a mode of automatic control of the set heating temperature. In the case of the automatic switch-off of the heating element 23, an audible click is heard and the indicator 24 is off.

The hydro-thermic heating device, comprising said elements, is a multifunctional device, which makes it possible, if such a need arises, to perform chemical and thermal sterilization of medical and dental instruments by fully dipping them into the liquid chamber.

Figure 17:
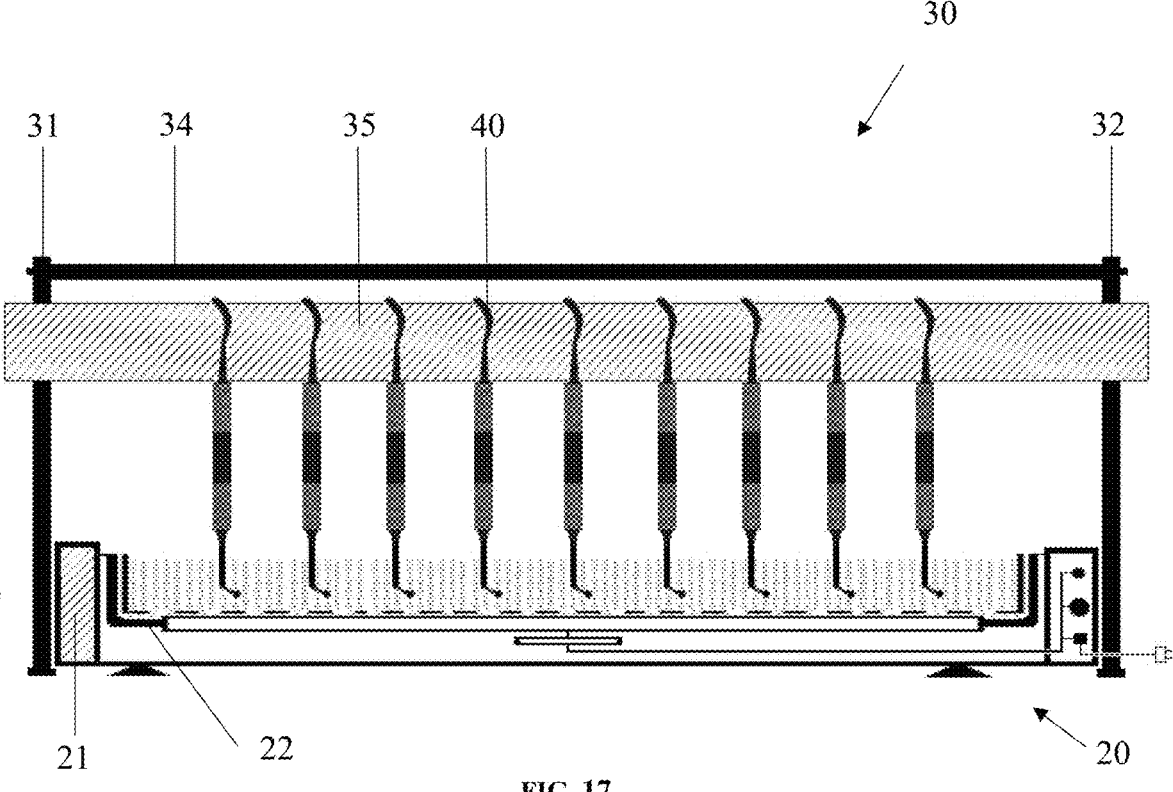
FIG. 17 shows a front view of a magnetic-panoramic stand for panoramic disposition and holding of restoration instruments located with respect to a hydro-thermic heating device according to an embodiment of the invention.

According to the inventive method, magnetic-panoramic stand 30 is used to ensure the heating of only the working parts of the restoration instruments (FIG. 17). Magnetic-panoramic stand 30 ensures panoramic disposition and secure holding of the restoration instruments 40 above hydro-thermic heating device 20, in particular above liquid chamber 22 so that only the working parts of the restoration instruments 40 are dipped into the liquid.

Figure 18:
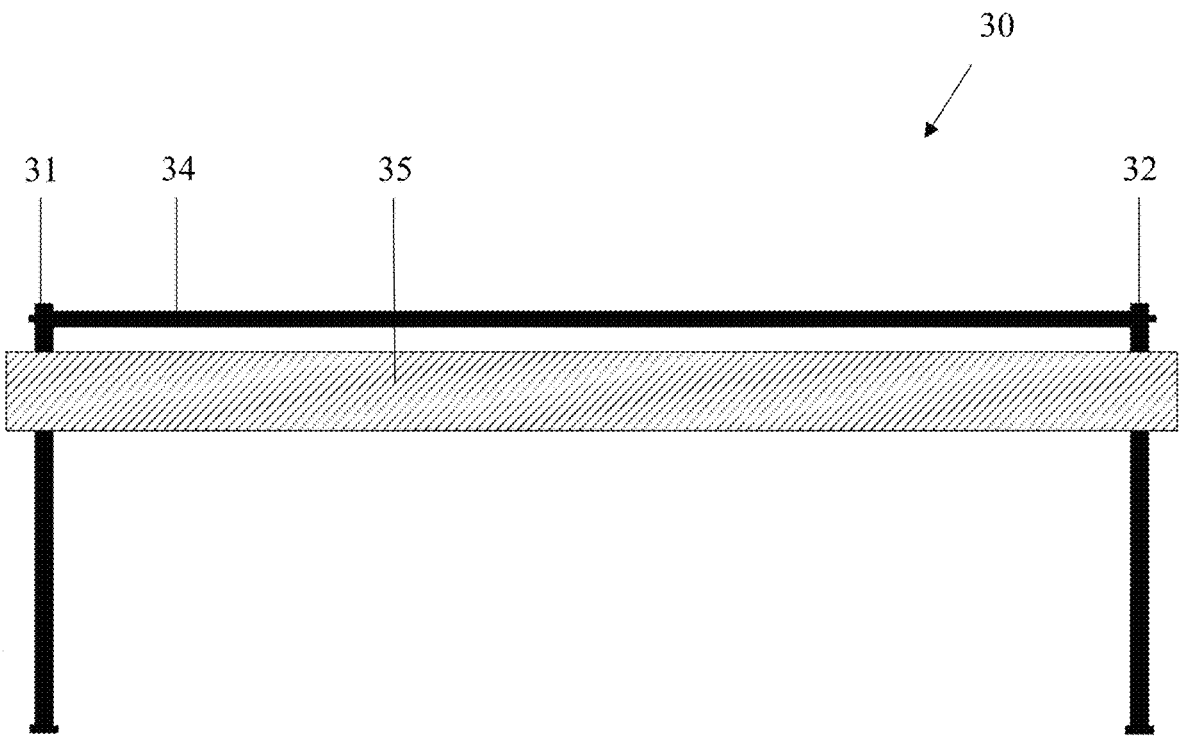
FIG. 18 shows a front view of a magnetic-panoramic stand for panoramic disposition and holding of medical instruments according to an embodiment of the invention.
Figure 19:
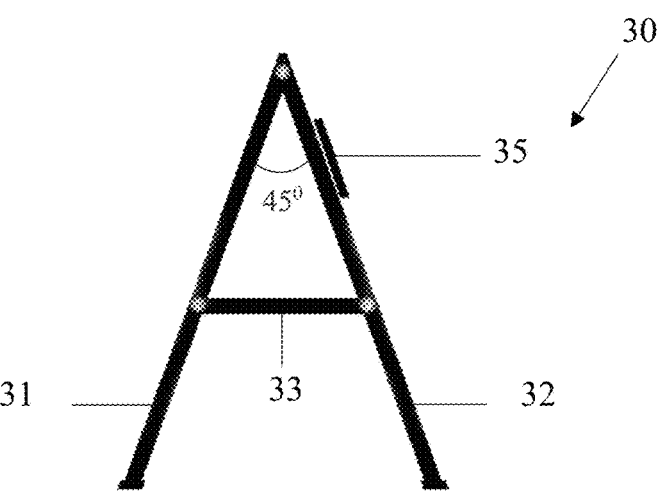
FIG. 19 shows a side view of a magnetic-panoramic stand for panoramic disposition and holding of medical instruments, including restoration instruments, according to an embodiment of the invention.

The magnetic-panoramic stand 30 comprises two pairs of legs wherein each pair of the legs is linked to each other at one end with the use of threaded studs so that each pair of the legs makes a bearing member 31, 32 of the stand (FIGS. 18, 19). Stoppers 33 representing two beams are attached to the bearing members 31, 32 of the stand thus preventing movement of the legs of the bearing members 31, 32 of the stand relative to each other. The bearing members 31, 32 of the stand are connected to each other by a fixing bar 34.

Figure 20:
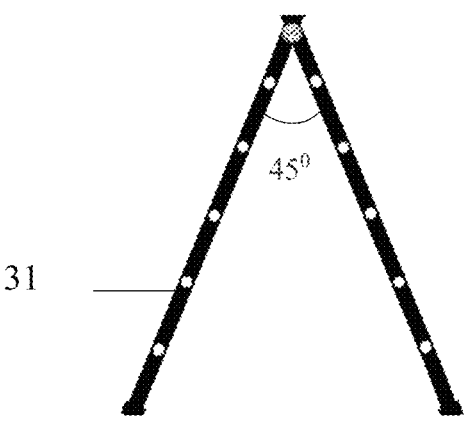
FIG. 20 shows a bearing part of a magnetic-panoramic stand for panoramic disposition and holding of medical instruments comprising holes for threaded studs according to an embodiment of the invention.
Figure 21:
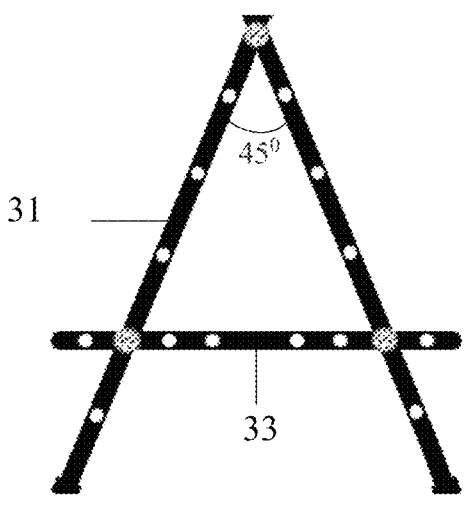
FIG. 21 shows a stopper of a magnetic-panoramic stand for panoramic disposition and holding of medical instruments comprising holes for threaded studs according to an embodiment of the invention.
Figure 22:
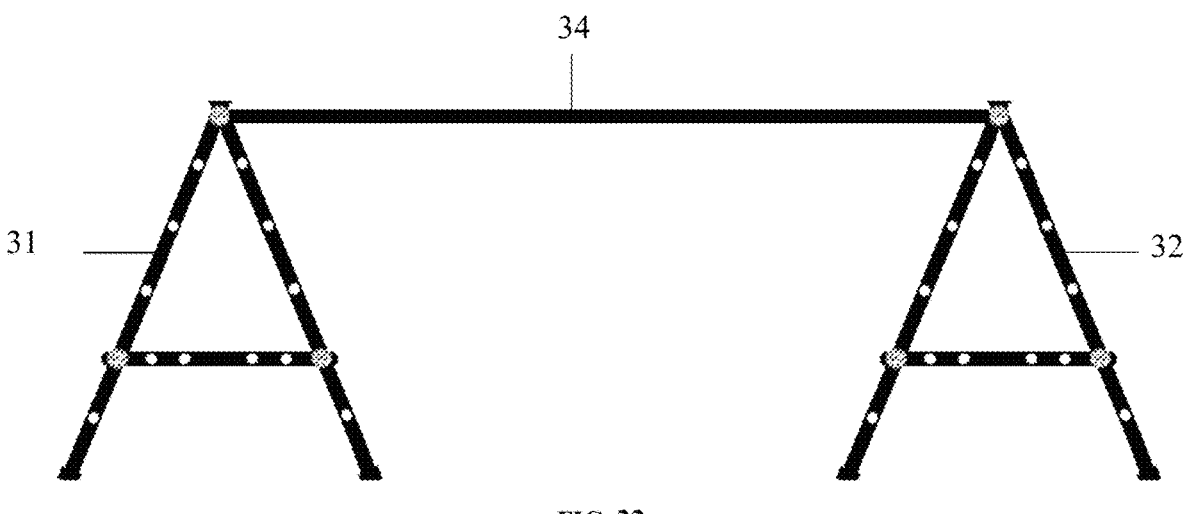
FIG. 22 shows bearing parts of a magnetic-panoramic stand for panoramic disposition and holding of medical instruments comprising holes for threaded studs according to an embodiment of the invention.
Figure 23:
FIG. 23 shows a cross-section of a bar element of a magnetic-panoramic stand for panoramic disposition and holding of medical instruments comprising holes for threaded studs according to an embodiment of the invention.

Elements of magnetic-panoramic stand 30 represent rod-type elements, for example, made of shaped tubes, which are of square, rectangular, round, or another form in cross-section and are connected to each other with the use of threaded studs, which ensures a possibility of multiple assembling-disassembling of the framework of the magnetic-panoramic stand 30. The rod-type elements can have the required number of holes for the threaded studs as shown in FIGS. 20-22. The bearing members 31, 32 are developed in FIG. 22 for illustrated purposes. The dismountable framework of the stand is made of high-quality medical stainless steel. The width and thickness of the rod-type elements is from 5 mm to 15 mm. FIG. 23 shows a cross-section of a rod-type element, which can represent, for example, a leg of one of the bearing members or magnet holder. Depending on the task at hand, parameters of the metal rod-type elements can be increased or decreased. Alternatively, the framework can be made of non-metallic-shaped tubes of different shapes and sizes.

Figure 24:
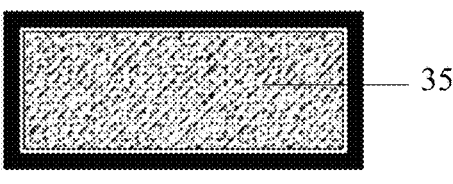
FIG. 24 shows a cross-section of a leg bearing part of a magnetic-panoramic stand for panoramic disposition and holding of medical instruments comprising magnet according to an embodiment of the invention.

Magnets 35 are hermetically installed inside the legs of the bearing members 31, 32 (FIG. 24). In particular, the magnets are isolated from the threaded holes that are formed in the legs, which excludes contact of the sterilized liquid with the magnets.

Figure 25:
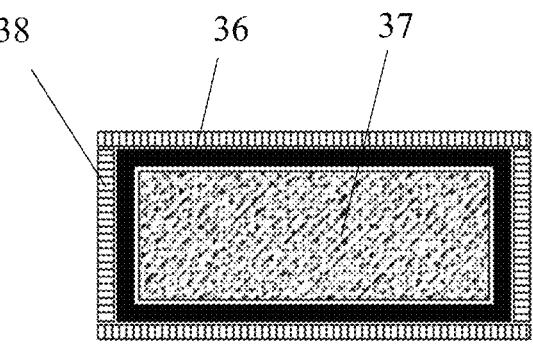
FIG. 25 shows a cross-section of magnet holders comprising housing, magnet, and insulating plates according to an embodiment of the invention.

The magnetic-panoramic stand also comprises a magnet holder 36, fixed at each end on the corresponding bearing member of the stand, and comprising the shaped metal housing and magnets 37 located in it (FIG. 25).

Thus, the magnetic holder 36 is fastened to the bearing members 31, 32 of the stand through the interaction of the magnets 35, installed in the legs of the bearing members 31, 32 of the stand, with the magnets 37 installed in the metal housing of the magnetic holder 36.

Figure 26:
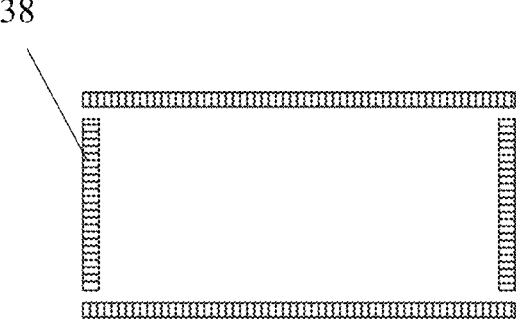
FIG. 26 shows a cross-section of insulating plates of magnetic holders according to an embodiment of the invention.

Additionally, removable sterile insulating plates 38 made of medical stainless steel are used to isolate the metallic or non-metallic magnet holder 36 from restoration instruments 40 (FIGS. 25, 26). Up to four 0.5-1.0-mm thick plates 38 or more, where applicable, are used to isolate one magnet holder 36. Parameters of insulating plates 38 corresponded to parameters of the magnet holder 36.

The removable insulating plates 38 and the restoration instruments 40 can be sterilized in a sterilizer while the magnet holders 36 are sterilized by a chemical method only. It is established that sterilization in autoclaves is more efficient as compared with chemical sterilization. When the sterilized instruments are positioned at the magnet holder surface, it may turn out that they shall be sterilized by different methods. Usage of the insulating plates 38 is preferable since sterilization of the insulating plates 38 and medical instruments can be carried out with the use of the same more efficient method.

Figure 27:
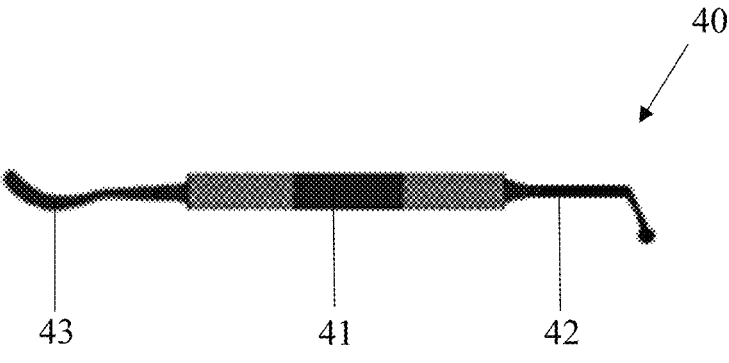
FIG. 27 shows a restoration instrument according to an embodiment of the invention.

At present different medical restoration instruments, 40 consisting of a handle 41, a handpiece 42, and a working part 43 are used during the composite tooth restoration (FIG. 27). The handpiece 42 represents a part of the instrument-connecting handle 41 with the working part 43. The handle 41 is designed for convenient holding of the instrument in the doctor's hand. The working part 43 is a part of the instrument, which is used by the doctor for performing whatsoever manipulations; for example, the working part of the instrument is used for applying and compacting an unpolymerized composite material portion on the polymerized surface of the adhesive or composite layers of the restored tooth. Normally, the restoration instrument 40 has two working ends with different forms and dimensions.

The length of the restoration instruments 40 is, on average, from 16 cm to 20 cm. The length of handle 41 is from 8 cm to 12 cm. Length of each working part 43 of the instrument is from 4 cm to 6 cm. The diameter of the handle 41 is, on average, 10 cm. The working part 43 is mainly made of medical stainless steel possessing magnetic properties. The handles 41 can be metallic and non-metallic. It is known that non-metallic and some metallic handles of the restoration instruments do not possess magnetic properties in which case attachment of the magnet holder 36 to the insulating plates 38 is made with the use of the handpiece 42 of the restoration instrument. Insulating metal plates 38 have a smooth surface, however, where applicable, the surface of plates 38 can have the form of working part and the handpiece 43, 42 of the medical restoration instruments 40 which additionally ensures reliability of their attachment.

The magnetic-panoramic stand can also have support configured to rotate the magnetic-panoramic stand in a horizontal plane and/or a vertical plane.

When assembling magnetic-panoramic stand 30 each pair of the legs of the bearing members 31, 32 are connected to each other by a threaded stud which is screwed into the aligned holes located at edges of the legs upperparts; thus a hinged-threaded connection between the front and rear legs of each bearing member 31, 32 is formed. Following that, the legs are moved apart so that an angle of about 45° is formed in the area of the hinged-threaded connection (FIG. 20). Removable non-slipping rubber pads are mounted on the lower parts of the legs.

Further, the legs are connected with each other at a selected angle of about 45° with the use of the stopper (FIG. 21). The stopper 33 is designed with a length from 10 cm to 20 cm and with a width up to 2 cm. Stopper 33 has rounded edges and several through-holes with a diameter of 3.8 mm. Preferably, the distance between the holes defining the angle between the legs is 1.5 cm. To fix the legs in the desired position stopper 33 is installed on the legs so that two holes of the stopper are aligned with two holes of the front and rear legs. Further, the said holes are connected by the threaded studs. Thus connected with each other and secured the front and rear legs represent A-shaped work and form the left bearing member 31 of the stand. The right bearing member 32 of the stand is assembled similarly (FIG. 22).

Figures 28, 29:
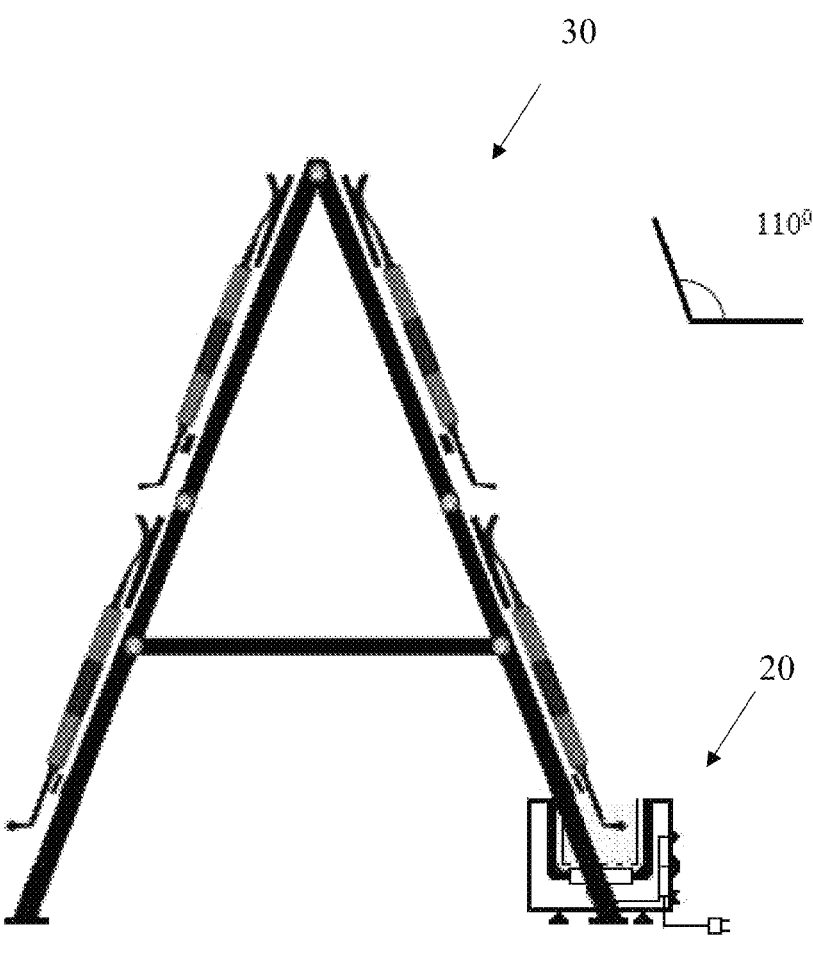
FIG. 28 shows a location of a magnetic-panoramic stand with restoration instruments with respect to a hydro-thermic heating device according to an embodiment of the invention.
FIG. 29 shows a location of a magnetic-panoramic stand with restoration instruments with respect to a hydro-thermic heating device according to an embodiment of the invention.
Figures 30, 31:
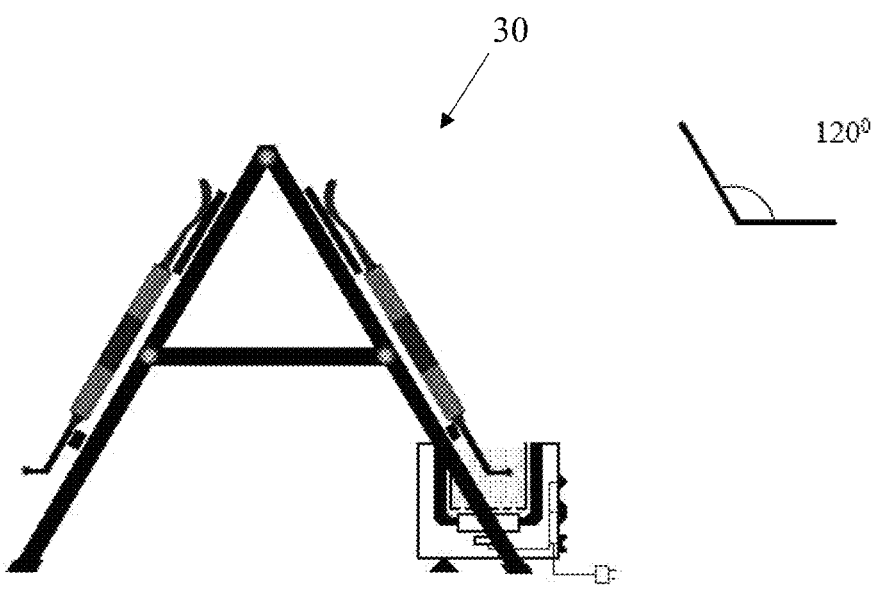
FIG. 30 shows a location of a magnetic-panoramic stand with restoration instruments with respect to a hydro-thermic heating device according to an embodiment of the invention.
FIG. 31 shows a location of a magnetic-panoramic stand with restoration instruments with respect to a hydro-thermic heating device according to an embodiment of the invention.
Figure 32:
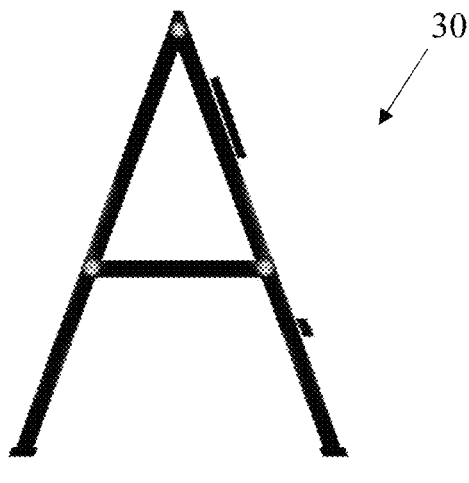
FIG. 32 shows a side view of a magnetic-panoramic stand with magnet holders arranged in two rows according to an embodiment of the invention.
Figure 33:
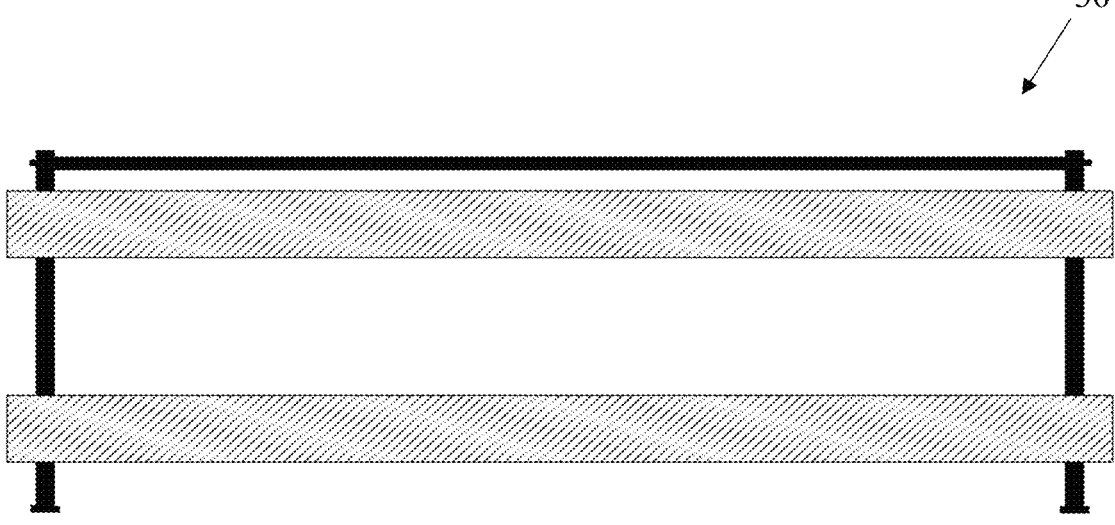
FIG. 33 shows a front view of a magnetic-panoramic stand with magnet holders arranged in two rows according to an embodiment of the invention.
Figure 34:
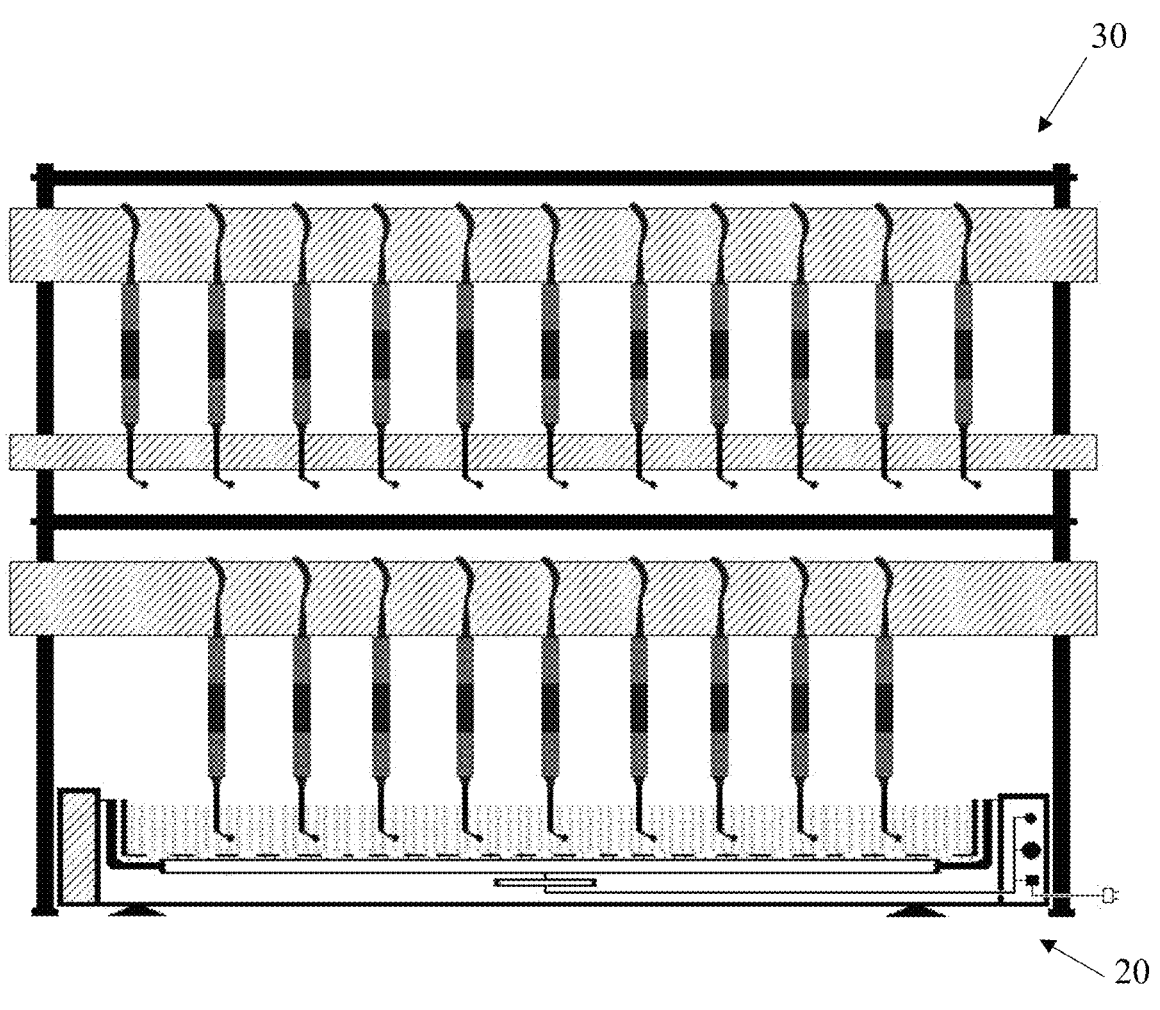
FIG. 34 shows a location of a magnetic-panoramic stand with respect to a hydro-thermic heating device with restoration instruments arranged in two rows according to an embodiment of the invention.
Figure 35:
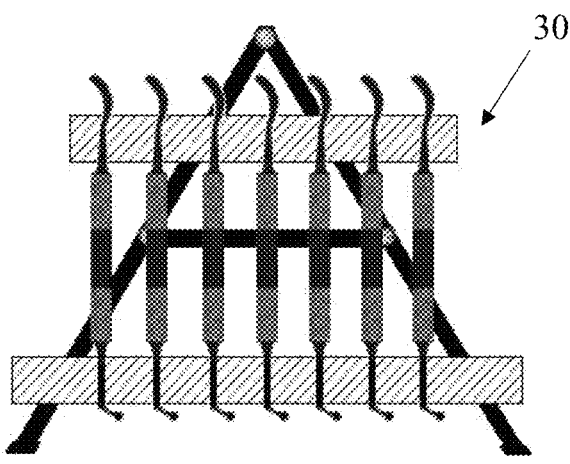
FIG. 35 shows the location of restoration instruments on one of the bearing parts of a magnetic-panoramic stand according to an embodiment of the invention.
Figure 36:
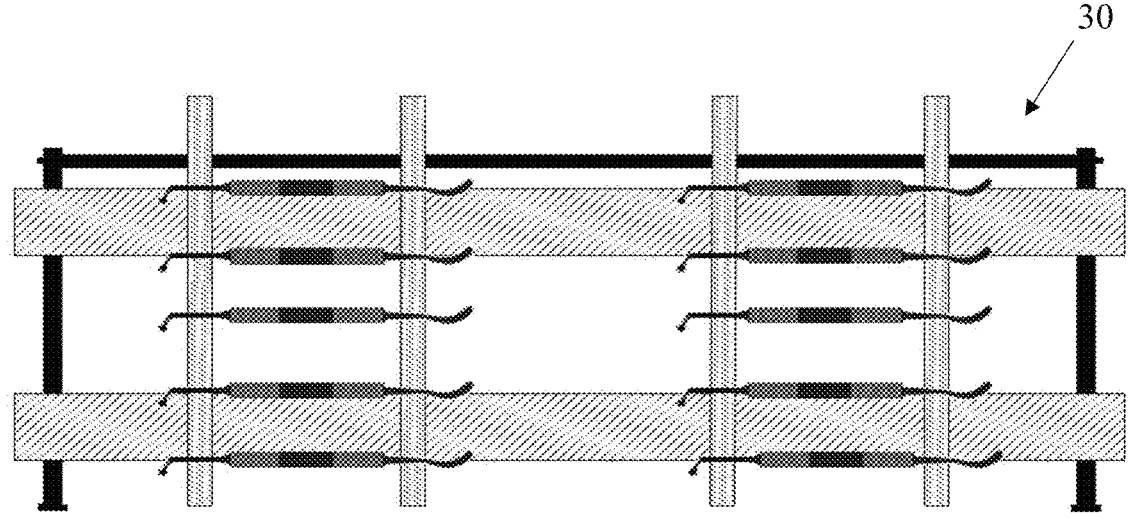
FIG. 36 shows the location of restoration instruments on a magnetic-panoramic stand in a horizontal position according to an embodiment of the invention.

The stopper 33 also makes it possible to adjust the tilt angle of the support legs from 40° to 180° owing to the availability of holes along its length. Thus to change the tilt angle of the support legs, the stopper is disconnected from the legs, then the legs are adjusted at the desired tilt angle, and the legs holes are aligned with the stopper holes spaced at a corresponding distance. In another embodiment, the stopper 33 can have holes along its length, connected with one another by a slit making it possible to change the angle between the legs without detachment of the stopper from the legs by shifting the studs between the holes along with the said skit. Thus changing the tilt angle of the legs against each other makes it possible to adjust the height and width of the dismountable framework of the stand (FIG. 28-31). Preferably, the front and rear legs of the framework have the same length. In another embodiment, the front and rear legs can differ in length which makes it possible to achieve different tilt angles for the front and rear legs (FIGS. 29, 31).

The fixing bar 34 with a length from 20 cm to 25 cm is used to connect and fix the right and left bearing members 31, 32 with one another. The fixing bar 34 is installed in the area of the hinged-threaded connection linking together the front and rear legs so that ends of the threaded studs fit freely into the holes formed at the fixing bar butt ends. Further, the studs are screwed all the way into the fixing bar 34 butt ends. As a result, right and left bearing members 31, 32 of the stand are connected to the horizontal fixing bar 34 at an about right angle.

Thus the front face part of the stand is restricted on the sides by the front legs, the rear, the rear face part is restricted on the sides by the rear legs and each of the flank sides of the stand is restricted on the sides by the front and rear legs. Preferably, the front face side of the stand is intended for panoramic disposition and reliable holding of the restoration instruments 40 above liquid chamber 22 of the hydrothermic heating device 20. The rear face part and flank sides of the stand are intended for panoramic disposition and reliable holding of the restoration instruments 40 which are not used and not heated in the process of the restoration works (FIGS. 28-31).

The holding of the restoration instruments 40 on the stand is ensured by the magnets 37 located in the shaped (hollow) metal housing of the magnet holder 36. In another embodiment, the housing of the magnet holder 36 can be made of plastic. The magnet holders 36 can be installed at each side of the stand 30 and/or in several rows (FIGS. 32-35). A number of the magnet holders 36 can be chosen depending on the number of the medical instruments 40 to be dispositioned on the stand 30. Length of the magnet holder 36 corresponds to distance between the respective legs of the bearing members 31, 32 or can be longer than it.

Each magnet holder, owing to its hollow shape, makes it possible to dispose of the magnets 37 inside it along its entire length. The butt end openings of the magnet holder 36 with magnets inside are tightly welded or closed by plastic plugs to exclude penetration of sterilization liquid inside its housing.

The magnet holder 36 is fastened to the bearing members of the stand 30 using the force of attraction of the magnets 37 placed inside its housing to the magnets 35 located inside the legs of the bearing members. The width of the magnet holders 36 should correspond to the length of the working part and the handpiece 43, 42 of the medical instrument 40. Preferably, the width of the magnet holder 36 is 4 cm, which makes it possible to securely fix both working part 43 and handpiece 42 of restoration instrument 40.

During layering elimination of defects of hard tooth tissues and dental arch according to the temperature balance concept by M. L. Melikyan, the temperature of all components (water-air, adhesive, composite portions, working parts of restoration instruments, polishing paste, etc.) should be within the body temperature range (in the normal condition).

According to the invention, the method of providing medical services according to the temperature balance concept by M. L. Melikyan is accomplished in the following way. When interacting with a patient's body in providing medical services, a system approach is used where all objects interacting with the patient's body, including instruments, fluids, and medical materials, are pre-heated up to a generally accepted normal value of the body temperature, in particular up to 36.6° C., prior to interaction with the patient's body.

The method of providing medical services according to the temperature balance concept, in particular, the performance of the layering composite tooth restoration according to the temperature balance concept by M. L. Melikyan is accomplished in the following way. The magnetic-panoramic stand 30 is assembled, and a desired angle between the front and rear legs of the bearing members 31, 32 is set. The liquid chamber of the hydro-thermic device 20 is filled with a liquid after which it is installed between the front legs of the bearing member of the magnetic-panoramic stand, and heating is switched on. The required restoration instruments 40 are disposed on the magnet holders 36 of the magnetic-panoramic stand 30. At that, the restoration instruments 40 to be heated are disposed on the magnet holders 36 so that their working parts 43 are dipped into the liquid chamber 22.

If the restoration instrument 40 on one magnet holder 36 is weakly attracted, then the second magnet holder is added. The second magnet holder is located below the first magnet holder on the front legs so that the first handpiece of the restoration instrument is located on the first magnet holder and the second handpiece is located on the second magnet holder (FIGS. 28-31).

The working part 43 of the restoration instrument 40 is dipped into the liquid chamber 22 to the depth up to 4 cm, at that the working element 43 surfaces should not touch walls of the liquid chamber 22, in particular, the end of the working part 43 of the restoration instrument 40 should not reach the bottom of the liquid chamber 22 by 1 cm. Distance between the handles 41 of panoramically disposed of the restoration instruments 40 should be a minimum of 1.5 cm. A doctor can individually establish the distance between the handles 41 taking into account the thickness of his/her forefinger and thumb. Thus, it makes it possible to easily retrieve the restoration instrument 40 and put it back on stand 30 without straining eyesight and finger. Thus the number of the restoration instruments 40 disposed on the magnetic-panoramic stand 30 depends on varying dimensions of the stand 30 and on individual requirements of the user. Length of the magnetic-panoramic stand 30 can be changed by an increasing distance between the pairs of the front legs, the width of the stand can be changed by an increasing distance between the side legs, and the height of the stand can be changed by increasing the length of the legs. Then the tooth preparation is made using water and air heated to the body temperature.

Ring 13 of the syringe is put on the ring finger of the hand so that the syringe with the acid is clasped to the palm at places upper, middle, and lower phalanges of the ring finger and small finger. Thus, the acid located at the syringe nozzle is heated to the user's body temperature in a few minutes.

Following that, an acid portion heated to the body temperature is extracted from the syringe and the heated acid portion is applied to the prepared tooth surface after which it is washed away by water heated to the body temperature and dried out by air heated to the body temperature.

Further, the adhesive portion is heated to the body temperature in the vessel for the adhesive, it is extracted from the vessel, and the heated adhesive portion is applied to the tooth surface, and it is blown out by air heated to the body temperature after which polymerization is performed. Further, according to the inventive method, a heated composite material portion is extracted using the heated working part 43 of the restoration instrument 40, and the heated composite material portion is applied to the polymerized surface of the tooth adhesive layer using the heated part of the restoration instrument, and after compacting polymerization of the composite layer is performed. Following that, the second and subsequent heated composite material portions are applied to the polymerized surfaces of the composite layers applied at previous stages with the use of the heated working part 43 of the restoration instrument 40. After compacting polymerization is performed.

At the final stage, after applying a required number of the composite layers and after grinding of the composite restoration, an extracted and heated polishing paste portion is applied to the restored tooth surface, and the tooth polishing is carried out with the use of the polishing paste.

Thus, the inventive method for the layering composite tooth restoration according to the temperature balance concept by M. L. Melikyan during the composite tooth restoration makes it possible to maintain the constant temperature of the composite material, in particular up to 36.6° C., which makes it possible to exclude thermal cycling stress of the composite material and perform the layering composite tooth restoration under conditions of the temperature balance. The heated composite material has improved properties, and namely better yield, plasticity, marginal adaptation, and manipulation parameters, thus its implementation considerably decreases the number of occurrences of large critical closed and strain restoration pores as well as critical zones in the composite restoration volume which is the main reason leading to the occurrence of cracks, micro-and-macro chipping of the composite restoration. Thus, the inventive method for the layering composite tooth restoration according to the temperature balance concept by M. L. Melikyan during the composite tooth restoration makes it possible to obtain a high-quality restoration with the prolonged service life.

It is necessary to note that according to the invention of the disclosed syringe, the hydro-thermic heating device for heating the working parts of the instruments, and the magnetic-panoramic stand can be used in different areas of medicine where implementation of the temperature balance concept by M. L. Melikyan can be useful.

This invention is not limited to the specific embodiments disclosed in the description for illustration purposes and covers all possible modifications and alternatives included in the scope of this invention defined by the claims.

The invention claimed is:

1. A method of layering composite tooth restoration, the method comprising:

heating an acid portion, a first composite material portion, a second and subsequent composite portion, and a polishing paste portion to a body temperature in corresponding syringes and heating an adhesive portion to a body temperature in a vessel;

heating a working part of a restoration instrument in a hydro-thermic heating device using a magnetic-panoramic stand for panoramic disposition and securely holding of the restoration instrument, wherein the magnetic-panoramic stand is configured to be positioned above the hydro-thermic heating device so that only the working part of the restoration instrument is dipped into the hydro-thermic heating device, performing a tooth surface preparation of a patient, using water and air heated to a body temperature, extracting, from the corresponding syringe, the acid portion heated to the body temperature, applying the heated acid portion to the prepared tooth surface, subsequently washing away the acid portion using the water heated to the body temperature and drying the tooth surface using an air heated to the body temperature, extracting, from the vessel, the adhesive portion heated to the body temperature, applying the heated adhesive portion to the dried tooth surface, blowing the adhesive portion using the air heated to the body temperature after which polymerization is performed to form a polymerized adhesive layer, extracting, from the corresponding syringe, the first composite material portion heated to the body temperature using the working part of the restoration instrument heated to the body temperature, applying the first heated composite material portion to the polymerized adhesive surface using the working part of the restoration instrument heated to the body temperature, and performing polymerization after compacting the first heated composite material portion to form a first polymerized composite layer, extracting, from the corresponding syringes, the second and subsequent composite material portion heated to the body temperature using the working part of the restoration instrument heated to the body temperature, applying the heated second and subsequent composite material portion to the first polymerized composite layer using the working part of the restoration instrument heated to the body temperature, and performing polymerization after compacting the second and subsequent composite material portions to form a second polymerized composite layer of the second and subsequent composite material, after grinding of the second polymerized composite layer, extracting, from the corresponding syringe, the polishing paste portion heated to the body temperature, polishing the tooth using the heated polishing paste portion.

2. The method according to claim 1, wherein the syringes are heated in a palm, wherein each syringe is held in the palm using a ring attached to a cap of the syringe.

3. The method according to claim 1, wherein the vessel for the adhesive is heated in the palm, wherein the vessel for the adhesive is held in the palm using the ring attached to a butt end of the vessel for the adhesive.

* * * * *